United States Patent
Hermes

(10) Patent No.: US 7,026,831 B2
(45) Date of Patent: Apr. 11, 2006

(54) METHOD AND DEVICE FOR MEASURING THE DIFFUSION LENGTH OF MINORITY CARRIERS IN A SEMICONDUCTOR SAMPLE

(76) Inventor: Uwe Hermes, 2267 NW. Overton St., #B, Portland, OR (US) 97210

( * ) Notice: Subject to any disclaimer, the term of this patent is extended or adjusted under 35 U.S.C. 154(b) by 0 days.

(21) Appl. No.: 10/514,665

(22) PCT Filed: May 15, 2003

(86) PCT No.: PCT/EP03/05086

§ 371 (c)(1),
(2), (4) Date: Nov. 15, 2004

(87) PCT Pub. No.: WO03/098197

PCT Pub. Date: Nov. 27, 2003

(65) Prior Publication Data

US 2005/0237080 A1    Oct. 27, 2005

(30) Foreign Application Priority Data

May 17, 2002  (DE) ................................ 102 21 937

(51) Int. Cl.
*G01R 31/302* (2006.01)
(52) U.S. Cl. .................... 324/752; 324/766; 324/750
(58) Field of Classification Search .............. None
See application file for complete search history.

(56) References Cited

U.S. PATENT DOCUMENTS

| | | | |
|---|---|---|---|
| 4,333,051 A | | 6/1982 | Goodman |
| 5,025,145 A | | 6/1991 | Lagowski |
| 5,663,657 A | | 9/1997 | Lagowski et al. |
| 6,917,039 B1 | * | 7/2005 | Nicolaides et al. ...... 250/341.1 |
| 6,922,067 B1 | * | 7/2005 | Van et al. .................... 324/752 |

FOREIGN PATENT DOCUMENTS

WO    WO 02/03053 A1    1/2002

OTHER PUBLICATIONS

Schroder, Dieter, Surface voltage and surface photo-voltage: history, theory and applications, review article. Meas. Sci. Technol. 12 (2001) R16-R31 2001 10P Publishing Ltd.

* cited by examiner

*Primary Examiner*—Vinh Nguyen
*Assistant Examiner*—Trung Q. Nguyen

(57) ABSTRACT

It is the goal of the invention to provide an improved method and an improved apparatus to measure the diffusion length of minority charge carriers in semiconductors. In particular, the method should be easy to implement. The method should yield higher measurement accuracy. The data analysis should be easy. The apparatus should be easy to use. This goal is achieved using the following procedure steps: Application of periodically alternating light of different wavelengths ($\lambda 1$, $\lambda 2$) to the semiconductor sample (28); Detection of the surface potential modulation caused by the application of the light, Adjustment of at least one of the light intensities (I1) in such a manner that the surface potential modulation disappears; and Determination of the diffusion length (L) of the minority charge carriers from the adjusted light intensities. An apparatus consists of a first and a second monochromatic light source (10, 14) with different wavelengths ($\lambda 1$, $\lambda 2$), means (18, 20, 22) to periodically apply the light of the first and second light source (10, 14) to the sample (28), means (30) to detect the surface potential of the sample (28), means (32) to detect the modulation of the surface potential of the sample, means (34, 36) to adjust the intensity of the light of at least one of the light sources (10) in such a manner that the modulation of the surface potential disappears and means to determine the diffusion length (L) of the minority charge carriers from the adjusted light intensities of the first and second light source (FIG. 1).

8 Claims, 3 Drawing Sheets

Drawing for an apparatus to implement the proposed method.

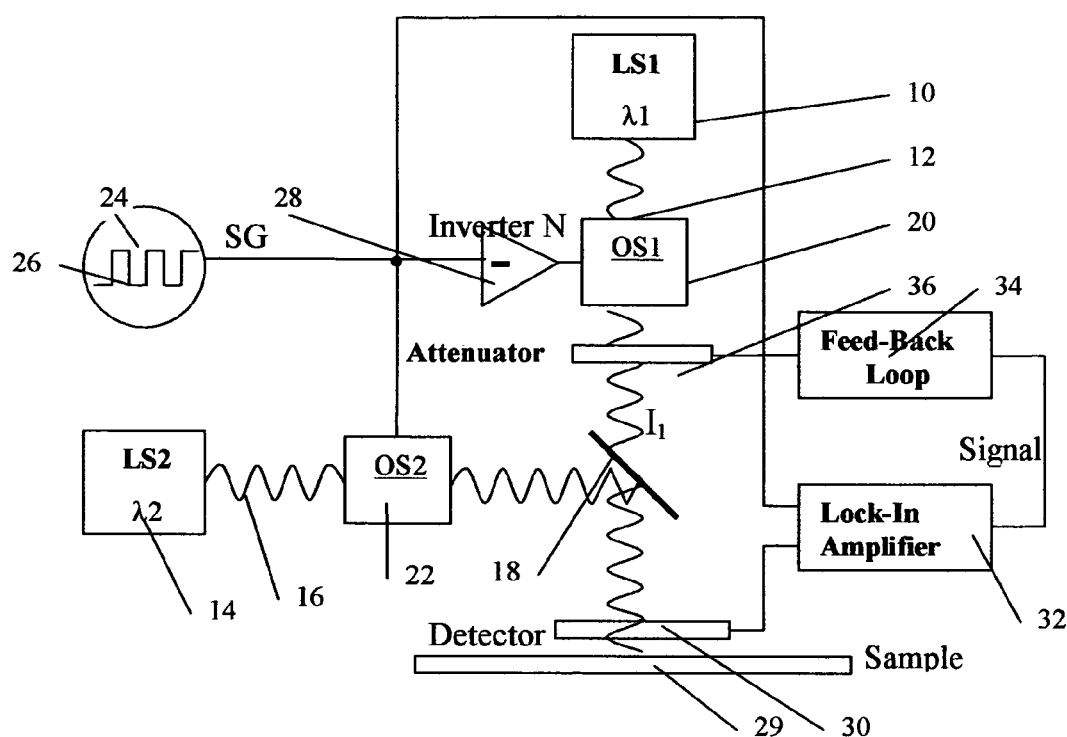
Fig. 1: Drawing for an apparatus to implement the proposed method.

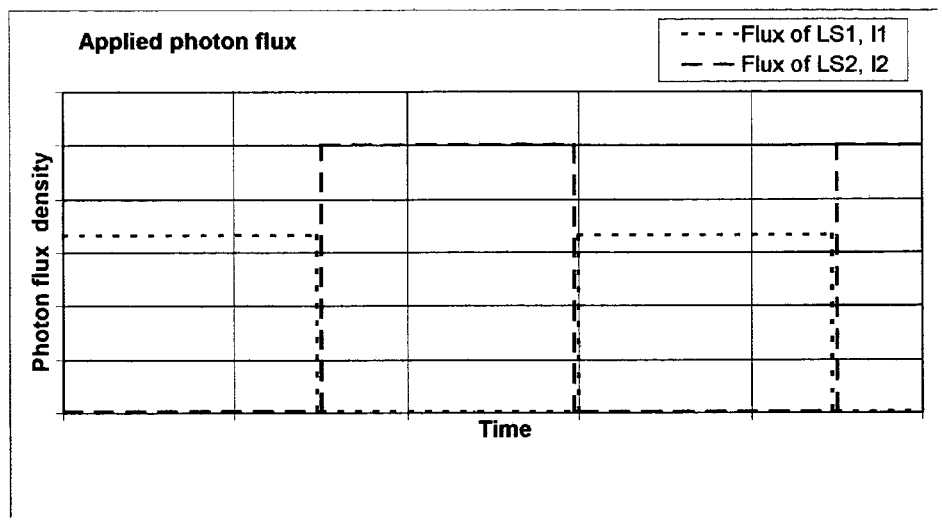
Fig. 2: Photon fluxes applied to the semiconductor sample (Rectangular function)
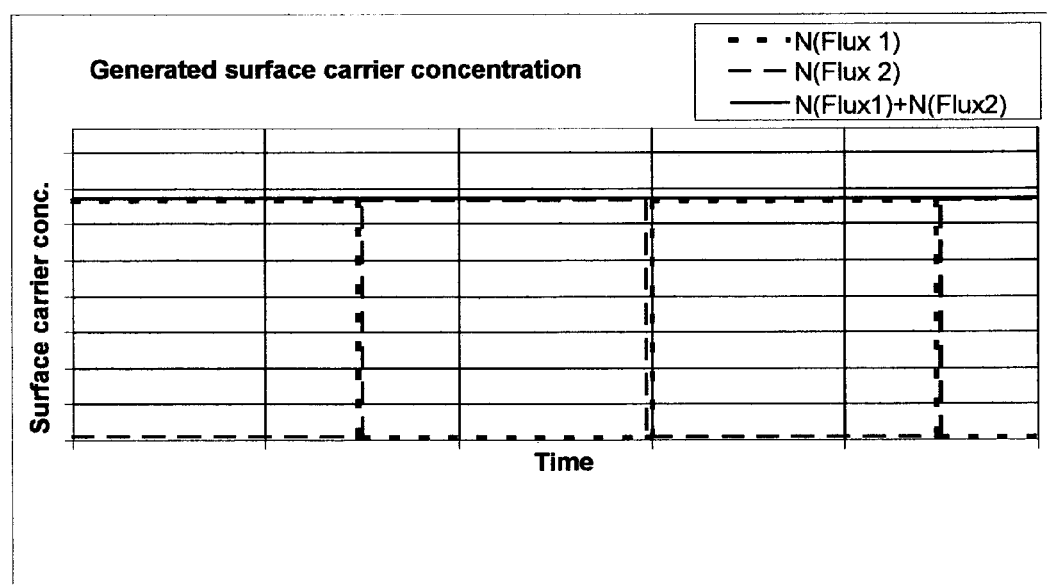
Fig. 3: Generated surface charge carrier concentration by the photon fluxes in Fig. 2

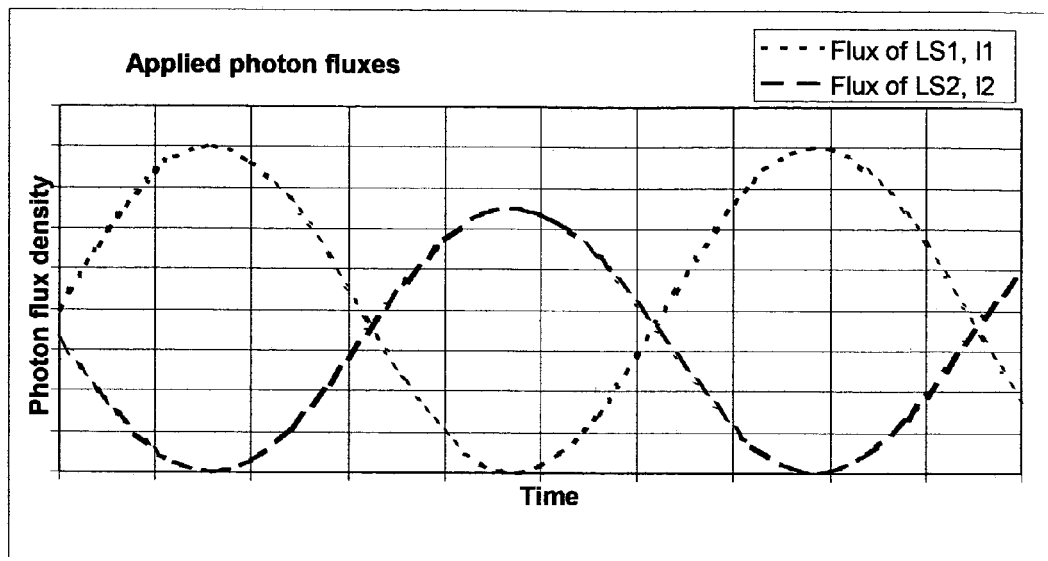
Fig. 4: Applied photon fluxes to the semiconductor sample (Sine function)
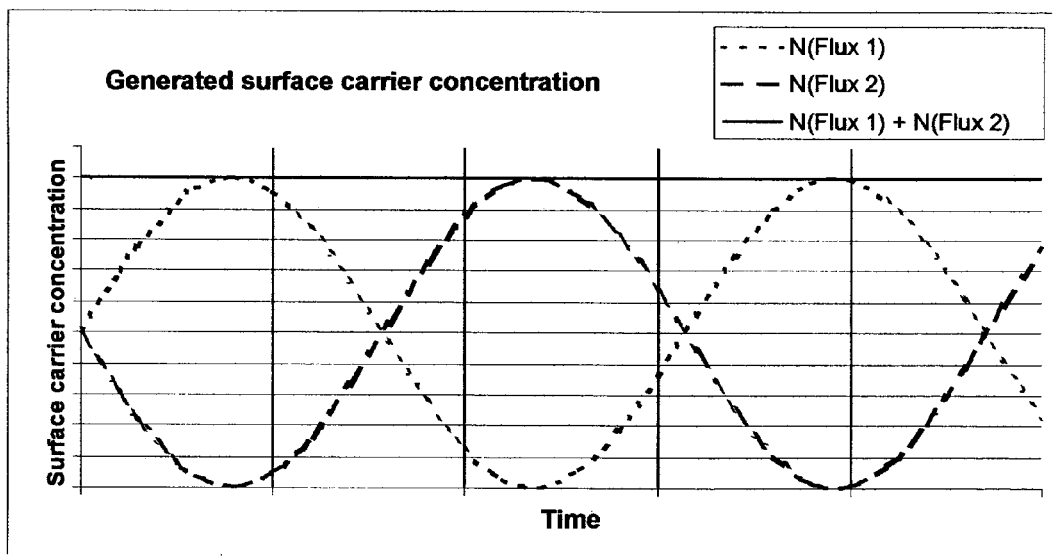
Fig. 5: Generated surface charge carrier density by the photon fluxes in Fig. 4

METHOD AND DEVICE FOR MEASURING THE DIFFUSION LENGTH OF MINORITY CARRIERS IN A SEMICONDUCTOR SAMPLE

The invention presents a method for measuring the minority charge carrier diffusion length in semiconductors. The invention describes furthermore an apparatus that implements said method.

The measurement of the diffusion length of minority charge carriers provides a way to characterize quality and contamination of semiconductors.

The invention is commercially applicable by developing and selling such an apparatus that measures the minority charge carrier diffusion length of semiconductor samples based on the invented method.

In a known measurement method (ASTM F 391-96 "Standard Test Methods for Minority Carrier Diffusion Length in Extrinsic Semiconductors by Measurement of Steady-State Surface Photovoltage", Method A) the semiconductor sample is exposed to modulated light. The resulting modulation of the surface potential of the semiconductor is measured for a number of light beams of different wavelength. During the measurements the photon flux intensity is adjusted in such a way that the same given surface potential modulation is achieved for each wavelength. The diffusion length of the minority charge carriers can be calculated from the obtained dependency between the photon flux and wavelength.

In another known method (ASTM F 391-96 "Standard Test Methods for Minority Carrier Diffusion Length in Extrinsic Semiconductors by Measurement of Steady-State Surface Photovoltage", Method B) the modulation of the surface potential is measured for a number of light beams of different wavelength. The photon flux, however, is kept constant for each wavelength while the different amplitudes of the surface potential modulation are measured. The minority charge carrier diffusion length is calculated from the wavelength dependency of the surface potential modulation amplitude.

Both methods assume a linear dependency between surface potential and photon flux. Therefore, these methods can only be applied under certain conditions that fulfill this assumption. That limits the intensity of the photon fluxes to small values. The linearity range has to be determined. The data evaluation is complicated. The measurement result is impacted by changes in time of material parameters that have an impact on the dependency between surface potential and light intensity. An example for such a parameter is the surface recombination velocity.

The invention has the goal to provide an improved method and an improved apparatus for measuring the minority charge carrier diffusion length.

In particular, the method should be easy to carry out. The method should provide improved measurement accuracy. The method's data analysis should be simple. The apparatus should be simple to use.

According to the invention, this goal is achieved by a method for measuring the diffusion length of minority charge carriers of a semiconductor sample, characterized by the following procedure steps:

(a) Application of periodically alternating light of different wavelengths to the semiconductor sample,
(b) Detection of the surface potential modulation caused by the application of light.
(c) Adjustment of at least one of the light intensities in such a manner that the surface potential modulation disappears, and
(d) Determination of the diffusion length of the minority charge carriers from the adjusted light intensities.

An apparatus to apply this method consists of a first and a second monochromatic light source with different wavelengths ($\lambda 1, \lambda 2$), means to periodically apply the light of the first and second light source to the sample, means to detect the surface potential of the sample, means to detect the modulation of the surface potential of the sample, means to adjust the intensity of the light of at least one of the light sources in such a manner that the modulation of the surface potential disappears and means to determine the diffusion length of the minority charge carriers from the adjusted light intensities of the first and second light source.

The application of light to the sample can be done using periodically alternating light of two different light sources of different wavelengths. However, the application can also consist of light from more than two light sources with an appropriate phase shift, e.g. a phase shift of 120 degrees for light of three different wavelengths.

The intensity of the light of each wavelength can be modified according to a steady function of time. It is also possible to modify the light intensities of each wavelength according to a rectangular function of time.

With such a method and such an apparatus, the measurement result is not impacted by a non-linear dependency between surface potential and light intensity. This results in a higher measurement accuracy.

The range of intensities for the photon fluxes can be chosen higher than in currently known methods. This causes not only a higher measurement accuracy, but also a smaller measurement time. With higher photon fluxes it is possible to measure the diffusion length of minority charge carriers of low resistivity materials that have not been possible to measure with the current methods.

Changes in material parameters (e.g. the surface recombination rate) during the sequential application of photon fluxes of different wavelengths are a significant cause for the limitation of the measurement accuracy in current methods. These changes have no influence in the proposed method since they are slow in comparison with the modulation of the light sources. Therefore a much higher accuracy is achieved in determining the diffusion length of minority charge carriers.

Another advantage of the invented method is that the measured signal of the surface potential does not need to be calibrated. Furthermore, inhomogenities in the illuminated spot on the sample do not affect the measurement results since in the adjusted state all light beams generate the same carrier concentration distribution on the surface. Therefore smaller spot sizes and a higher spatial resolution can be achieved.

Details of the invention are part of further sub-claims.

An example of an implementation of the invented method is described using the following drawings:

FIG. 1 is a schematic drawing of an apparatus for measuring the diffusion length of the minority charge carriers of a semiconductor sample.

FIG. 2 shows the time dependent intensity of two periodically alternating photon fluxes in the adjusted state. The photon fluxes are modified according to a rectangular function of time.

FIG. 3 shows the time-dependent surface charge carrier concentrations caused by the two photon-fluxes shown in FIG. 2 and the sum thereof.

FIG. 4 shows the time-dependent intensity of two photon fluxes in the adjusted state. The photon fluxes are modified according to sine functions of time with a phase shift of 180° to each other.

FIG. 5 shows the time-dependent surface charge carrier concentrations generated by the photon fluxes in FIG. 4 as well as the sum thereof.

In FIG. 1, a first monochromatic light source is referred to as (10). The light source (10) emits a light beam (12) of wavelength $\lambda_1$. A second light source is referred to as (14). Light source (14) emits a light beam (16) of wavelength $\lambda_2$. The light beams (12) and (16) are perpendicular to each other. At the cross over of the light beams (12) and (16) is a semi-transparent mirror (18), forming an angle of 45° with each light beam (12) and (16). This semi transparent mirror superimposes the light beams (12) and (16). Half of light beam (12) passes through the semi transparent mirror (18). Half of the light beam (16) is reflected at the semi transparent mirror under an angle of 90° and superimposed to the passing light beam (12).

An optical switch (20) is placed in the optical path of the light beam (12). This optical switch attenuates the light beam according to a control signal. Such optical switches are readily available and therefore not described in more detail. Another optical switch (22) is placed in the optical path of light beam (16). Signal generator (24) controls the optical switches (20) and (22) in opposite phase to each other. The control signal can be a rectangular function as it is suggested in FIG. 1. However, the control signal may as well be a sine function, which would result in an intensity modulation as illustrated in FIG. 4. The optical switch (20) is controlled by the signal coming from the inverter (28), which inverts the signal coming from the signal generator (24). The optical switch (22) is controlled by the signal coming directly from the signal generator 24. Therefore, the light beams (12) and (16) are controlled by the optical switches (20) and (22) in opposite phase to each other as it is illustrated in FIGS. 2 and 4.

Each light beam generates a corresponding concentration of surface charge carriers and thus a corresponding surface potential. The surface potentials generated by the light beams (12) and (16) are superimposed. The surface potential generated by light beam (12) of wavelength $\lambda_1$ is smaller than the surface potential generated by light beam (16) of wavelength $\lambda_2$, when both light beams have the same photon flux intensity.

The surface potential is measured at the spot where the light beams (12) and (16) hit the surface of the semiconductor sample (29), using a detector (30). First, the surface potential is modulated as a result of the difference in surface charge carrier generation between the two light beams (12) and (16). The surface potential is e.g. higher when light beam (12) is at its maximum intensity and smaller, when light beam (16) is at its maximum intensity. Sinusoidal modulation of the light beams results in a sinusoidal modulation of the surface potential. The signal of detector (30) is fed into a Lock-In amplifier (32). The Lock-In amplifier (32) is synchronized by the signal of the signal generator (24). The Lock-In amplifier provides a control signal, the sign of which depends on the phase (0° or 180°) of the detector signal. This control signal is fed into a feedback loop (34). Said feedback loop controls an optical attenuator (36) that is placed in the optical path of light beam (12). Using the attenuator (36), the photon flux intensity $I_1$ of the first light beam (12) is adjusted in such a manner, that the surface potential modulation disappears.

This results in a situation illustrated in FIG. 2 and FIG. 3 or FIG. 4 and FIG. 5.

FIG. 2 shows the modulation of the first light beam by a rectangular function. The modulation of the second light beam is according to a second rectangular function (42). Both rectangular functions are in opposite phase to each other. This results in a modulation of surface charge carriers in the semiconductor sample (29). The feedback-loop (34) controls the amplitude of the first light beam (12) in such a way, that a constant, unmodulated surface charge carrier concentration (and hence a constant surface potential) is achieved. FIG. 3 illustrates this constant concentration of surface charge carriers as a horizontal line (44).

FIG. 4 shows sine functions (46) as modulation for the intensities of the two light beams. The first light beam (12) has a smaller amplitude than the second light beam (16). The modulation of the second light beam (16) is displayed as a sine function (48) with a phase shift of 180° to sine function (46). The surface charge carrier concentration modulation resulting from light beam (12), shown as curve (50), however, is a function of the same amplitude as the surface charge carrier concentration modulation caused by light beam (16), shown as curve (52), only with a 180° phase shift. Light beam (12) is more "effective". The combined concentration of surface charge carrier modulation is constant in time and shown in FIG. 5 as horizontal line (54).

This is the adjusted state. In this adjusted state, the intensities are in a certain ratio to each other, which is measured. From this ratio $I_1/I_2$ it is possible to calculate the diffusion length of the minority charge carriers using the relation $$L = \frac{d_2 \frac{I_1}{I_2} - d_1}{1 - \frac{I_1}{I_2}},$$

where $d_1$ and $d_2$ denote the penetration depths for light of wavelength $\lambda_1$ and $\lambda_2$ respectively.

What is claimed is:

1. Method to determine the diffusion length (L) of minority charge carriers in a semiconductor sample, comprising the procedure steps of:
   (a) Periodically alternating application of light beams of different wavelengths to the semiconductor sample,
   (b) Detection of the modulation of the surface potential of the semiconductor sample caused by the application of the light,
   (c) Adjustment of at least one light intensity in such a manner that the modulation of the surface potential disappears, and
   (d) Determination of the diffusion length of the minority charge carriers from the adjusted light intensities.

2. Method as defined in claim 1, where in procedure step (a) two light beams of different wavelengths ($\lambda_1$, $\lambda_2$) are applied periodically alternating to the semiconductor sample.

3. Method as defined in claim 1, where in procedure step (a) the light intensities of the applied wavelengths are modified according to steady functions of time.

4. Method as defined in claims 1 or 2, where in procedure step (a) the light intensities of the applied wavelengths are modified according to a rectangular function of time.

5. Method as defined in claims 1, 2, 3 or 4, wherein the diffusion length (L) of the minority charge carriers is determined from the ratio of each pair of two adjusted light intensities $I_j$ and $I_k$ according to the formula $$L = \frac{d_k \frac{I_j}{I_k} - d_j}{1 - \frac{I_j}{I_k}},$$

where $d_j$ is the penetration depth of light with a wavelength $\lambda_j$ and $d_k$ is the penetration depth of light with a wavelength $\lambda_k$.

6. Apparatus to measure the diffusion length of minority charge carriers in a semiconductor sample (28) to implement the method defined in claim 1, comprising a first and a second monochromatic light source (10, 14) with different wavelengths (λ1, λ2), means (18, 20, 22) to periodically apply light of the first and second light source (10, 14) to the sample (28), means (30) to detect the surface potential of the sample (28), means (32) to detect the modulation of the surface potential of the sample, means (34, 36) to adjust the light intensity of at least one of the light sources (10) in such a manner that the modulation of the surface potential disappears and means to determine the diffusion length (L) of the minority charge carriers from the adjusted light intensities of the first and second light source (FIG. 1).

7. Apparatus as defined in claim 6, wherein
(a) the two light sources (10,14) each send light of different wavelength (12,16) and the optical pathways of these two light rays (12,16) are combined with a semitransparent mirror (18) for the application of light on the semiconductor sample (28), and
(b) each of these optical paths contains an optical switch (20,22), controlled by the signal of a signal generator (24) in such a manner, that the application is periodically alternating between the two light sources.

8. Apparatus according to claim 7, wherein
(a) the means to determine the surface potential of the semiconductor sample comprising a detector (30) which is close to the sample surface and located in the spot of the applied light beams and which is sensitive to the surface potential of the sample,
(b) the signal of said detector (30) is fed into a lock-in amplifier (32) which is synchronized by the signal of the signal generator (24), and
(c) the output signal of the Lock-In-Amplifier (32) is fed into a feedback loop (34) which controls an attenuator (36) that is located in the optical path of one of the light sources (10) in order to achive zero surface potential modulation.

* * * * *